United States Patent [19]

Knox et al.

[11] Patent Number: 4,775,762

[45] Date of Patent: Oct. 4, 1988

[54] NOVEL (1H-1,2,3-TRIAZOL-1-YL)PYRIDINES

[75] Inventors: Ingrid L. Knox, Antioch, Calif.; Richard B. Rogers, Midland, Mich.

[73] Assignee: The Dow Chemical Company, Midland, Mich.

[21] Appl. No.: 49,196

[22] Filed: May 11, 1987

[51] Int. Cl.$^4$ ............................................ C07D 401/04
[52] U.S. Cl. .................................... 546/276; 514/340
[58] Field of Search ......................................... 546/276

[56] References Cited

U.S. PATENT DOCUMENTS 4,474,599  10/1984  Rogers et al. ........................ 546/276
4,606,757   8/1986  Malhotra et al. .................... 546/270

OTHER PUBLICATIONS

Huisgen et al., CA vol. 71, 81296s.
Banks et al., *J. C. S. Perkin I*, 1972, 2964–2970.
Lucacchini et al., CA 91:204219s.
Banks et al., *J. C. S. Perkins I*, 1974, 2479–2482.
Livi et al., CA 91:20407v.
Ahramovitch et al., *J.O. Chem.* vol. 40, No. 11, 1975, 1541–1547.
Finley Triazoles 1.2.3, p. 4, John Wiley & Sons.
Huisgen et al., *Chemische Ber.* 98 1138–1152 (1965).

*Primary Examiner*—Jane T. Fan
*Attorney, Agent, or Firm*—D. Wendell Osborne

[57] ABSTRACT

Pyridine ring substituted (1H-1,2,3-triazol-1-yl)pyridines were prepared and found to have insecticidal utility. 2-Chloro-6-(1H-1,2,3-triazol-1-yl)pyridine, for example, was prepared from 2-azio-6-chloropyridine and methyl propiolate by sequential condensation, hydrolysis, and decarboxylation and found to control aster leafhoppers.

17 Claims, No Drawings

NOVEL (1H-1,2,3-TRIAZOL-1-YL)PYRIDINES

BACKGROUND OF INVENTION

The present invention relates to novel (1H-1,2,3-triazol-1-yl)pyridines that are unsubstituted or are substituted only on the pyridine moiety.

(N-Azolyl)pyridines in general are a little known class of compounds and (1H-1,2,3-triazol-1-yl)pyridines having no substituents in the triazole moiety have not been reported. A number of (1H-1,2,3-triazol-1-yl)pyridines having hydrocarbon type substituents in the 3- and 4-positions of the triazole moiety and their utility as herbicides have been disclosed in U.S. Pat. No. 4,474,599. A few other (1H-1,2,3-triazol-1-yl)pyridines having substituents on the triazole moiety are also known. A variety of 1-(substituted phenyl)-1,2,3-triazoles are known and have been reported to reduce the feeding of insects in U.S. Pat. No. 4,499,280.

SUMMARY OF THE INVENTION

A new class of (1H-1,2,3-triazol-1-yl)pyridines optionally having substituents on the pyridine ring, but being unsubstituted on the triazole ring, has now been discovered. The compounds have insecticidal properties.

The compounds of the present invention are the (1H-1,2,3-triazol-1-yl)pyridines of the formula

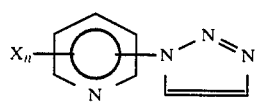

Formula I wherein
each X independently represents F, Cl, Br, $C_1$–$C_4$ alkyl, $OR^1$, $SR^1$, $SOR^1$, $SO_2R^1$, $NH_2$, $NHR^1$, $NR^1_2$, $CY_3$, $CHY_2$, CN, $NO_2$, $CO_2R^2$, or phenoxy containing up to three substituents selected from F, Cl, Br, $C_1$–$C_4$ alkyl, and $CF_3$;
each Y independently represents Cl or F;
$R^1$ represents $C_1$–$C_6$ alkyl, $C_3$–$C_6$ alkenyl, or $C_3$–$C_6$ cycloalkyl;
$R^2$ represents H, $C_1$–$C_6$ alkyl, $C_3$–$C_6$ alkenyl, $C_3$–$C_6$ cycloalkyl, $C_1$–$C_4$ alkoxy $C_2$–$C_3$ alkyl, $NH_2$, NH $C_1$–$C_4$ alkyl, or $N(C_1$–$C_4$ alkyl$)_2$; and
n represents 0, 1, 2, 3, or 4.

The compounds can be prepared from the corresponding azidopyridines by the steps of condensing with an ester of propiolic acid, hydrolyzing with an alkali metal hydroxide, and decarboxylating with heat. Alternatively, they can be prepared by thermally condensing the corresponding azidopyridine with vinyl acetate.

DETAILED DESCRIPTION OF THE INVENTION

The compounds of the invention are those of Formula I wherein X, Y, $R^1$, $R^2$, and n are as defined in the Summary of the Invention. The X moieties present in compounds wherein n is 2, 3, or 4 must, of course, be sterically and chemically compatible. The compounds of Formula I wherein X represents F, Cl, Br, $CH_3$, $OCH_3$, $SCH_3$, $CF_3$, or CN and n represents 1, 2, or 3 are preferred. The compounds of Formula I wherein at least one of X represents $CF_3$ are further preferred as are those wherein at least one of X represents F, Cl, or Br. Another preferred embodiment of the invention is those compounds of Formula I wherein the triazol-1-yl moiety is at the 2- or 6-position of the pyridine ring. The compounds 2-(1H-1,2,3-triazol-1-yl)-5-(trifluoromethyl)pyridine, 2-fluoro-6-(1H-1,2,3-triazol-1-yl)-pyridine, and 2-chloro-6-(1H-1,2,3-triazol-1-yl)-pyridine are especially preferred.

The term "alkyl" as used herein refers to all possible isomeric forms of moieties with the empirical formula $C_mH_{2m+1}$ and alkenyl and cycloalkyl refer to all possible isomeric forms of moieties with the empirical formula $C_mH_{2m-1}$ containing one double bond and one ring, respectively. The term "halo" refers to fluoro, chloro, bromo, or iodo.

The compounds of the present invention are generally prepared by condensation of an azidopyridine of Formula II, wherein X, Y, R, and n are defined as in the Summary of Invention, with a $C_1$–$C_6$ alkyl ester of propiolic acid and subsequent hydrolysis and decarboxylation of the alkyl ester. Each step of the process is carried out under conditions conducive to the reaction involved. The process can be depicted as follows:

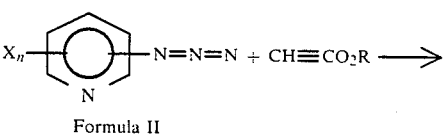

Formula II

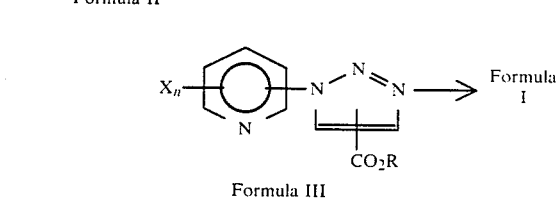

Formula III

The condensation is usually accomplished by refluxing a solution of the compound of Formula II and the alkyl propiolate in a solvent boiling between about 45° C. and 150° C., such as chloroform, for several days. Alternatively, mixtures of the reactants can be heated at about 120°–150° C. for a few minutes. The intermediates of Formula III, which consist of a mixture of the two possible isomers, are then generally recovered by evaporation of the volatile components of the mixture and cooling. These intermediates can be carried forward in crude form or can be purified by conventional methods, such as recrystallization or chromatography, before further use. Either isomer or a mixture of the isomers can be employed to prepare compounds of Formula I. Hydrolysis and decarboxylation are typically accomplished by treating the intermediates of Formula III with at least two molar equivalents of an alkali metal hydroxide, such as potassium hydroxide, in a solvent, such as isopropyl alcohol, and allowing the mixture to stand until the reaction is substantially complete. A strong acid, such as hydrochloric acid, and water are added and the solid that forms is collected by filtration and/or by extraction with a solvent, such as methylene chloride, followed by evaporation of the solvent from the extract. The carboxylic acid obtained is usually decarboxylated by refluxing in a solvent, such as xylene, until the evolution of carbon dioxide ceases. About 2 to 10 hours is required. The solvent is then generally removed by evaporation under reduced pressure to obtain the crude product of Formula I, which can be purified by conventional means, such as recrystallization from a solvent, sublimation, or chromatography.

The compounds of Formula I can generally be obtained more directly by condensation of an azidopyridine of Formula II with vinyl acetate. The compound of Formula II and an excess of vinyl acetate are generally combined and heated under conditions conducive to condensation until a significant quantity of the desired compound of Formula I forms. Heating at reflux for several days is typical. The product is recovered by conventional means, such as extraction and recrystallization.

Many of the compounds of Formula I can also be prepared by first preparing a precursor compound of Formula I, such as a compound of Formula I wherein X is bromo, chloro, fluoro, cyano, or nitro and subsequently converting this to the desired compound of Formula I using conventional transformations known to those skilled in the art of pyridine chemistry. For example, the compound of Formula I where Xn is 2-fluoro can be converted to compounds of Formula I wherein Xn is 2-$C_1$-$C_6$ alkyl, 2-$OC_1$-$C_6$ alkoxy, 2-$SC_1$-$C_6$ alkylthio, 2-phenoxy (optionally substituted), 2-amino, and 2-mono- or di-($C_1$-$C_4$ alkyl)amino by nucleophilic displacement using the appropriate reagents.

The azidopyridines of Formula II can generally be prepared by conventional diazotization methods from the corresponding hydrazinopyridines, usually with sodium nitrite and hydrochloric acid in aqueous media. Other known diazotization methods can also be employed. The hydrazinopyridines, in turn, can usually be prepared from known, appropriately substituted halopyridines by treatment of the halopyridines with hydrazine. Certain azidopyridines of Formula I are also preparable by the reaction of known, appropriately substituted halopyridines with sodium azide or by diazotization or appropriate aminopyridines in the presence of sodium azide. Conventional methods are employed. These methods of preparing compounds of Formula II can be summarized by the following equations wherein X, n, and Y are defined as in the Summary of the Invention.

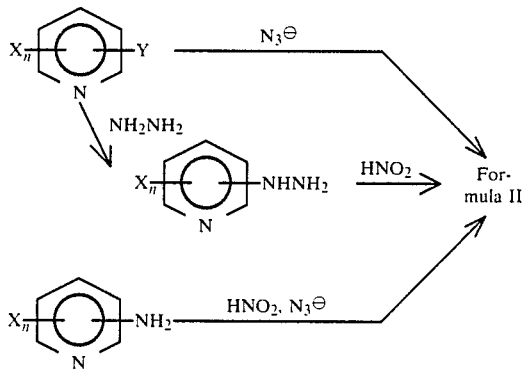

The compounds of Formula I are useful as insecticides for the control of aster leafhopper and related insects. The compounds are somewhat systemic in plants and are generally lethal to susceptible insects on ingestion of treated plants or the fluids of treated plants.

The following examples serve to illustrate the invention and should not be interpreted as limiting the claims.

EXAMPLE 1

Preparation of 2-Chloro-6-hydrazinopyridine and Certain Analogs 2,6-Dichloropyridine (44.40 g, 0.30 mol) was added to a stirring mixture of 35.09 g (0.70 mol) of hydrazine monohydrate in 100 ml of dimethyl sulfoxide. The mixture was heated at 65° C. for 30 hours and was then cooled and poured onto ice. The resulting solid was filtered, washed with water, and dissolved in ether. The etherial solution was dried over magnesium sulfate and stripped of solvent. The residue was triturated in pentane and filtered to yield 32.6 g (76 percent of theory) of off-white, fluffy solid product; m.p., 113°–115° C. NMR (CDCl$_3$/DMSO-d$^6$): $\delta$7.72 (s, 1H); $\delta$7.53 (t, 1H); $\delta$6.89 (d, 1H); $\delta$6.62 (d, 1h); $\delta$4.00 (s, 2H).

The following were prepared analogously and analyzed by nmr spectroscopy: 2-bromo-6-hydrazinopyridine, m.p. 112°–114° C. (from 2,6-dibromopyridine); 2-fluoro-6-hydrazinopyridine, m.p. 74°–76° C. (from 2,6-difluoropyridine); 2-hydrazino-6-(trifluoromethyl)pyridine, m.p. 62°–64° C. (from 2-chloro-6-(trifluoromethyl)pyridine; 3-hydrazino-5-(trifluoromethyl)pyridine, pale yellow solid (from 3-fluoro-5-(trifluoromethyl)pyridine); 4-hydrazino-2,3,5,6-tetrachloropyridine, m.p. 180°–181° C. (from pentachloropyridine).

EXAMPLE 2

Preparation of 2-Azido-6-chloropyridine and Certain Analogs

A mixture of 25 g of 2-chloro-6-hydrazinopyridine (0.17 mol) and 60 ml (0.74 mol) of concentrated hydrochloric acid in 200 ml of water and 100 ml of ether was cooled to 5° C. A solution of 13.22 g (0.19 mol) of sodium nitrite in 20 ml of water was added dropwise, keeping the temperature below 9° C. The mixture was stirred for two hours and then the organic phase was separated. The aqueous phase was extracted with ether. The ethereal solutions were combined, washed with water, dried over magnesium sulfate, and stripped of solvent. The residue was dissolved in a 50/50 mixture of hexane and methylene chloride. This was filtered through a pad of silica gel. The filtrate was concentrated under reduced pressure and the residue was recrystallized from hexane to yield 12.3 g (46 percent of theory) of cream solid product; m.p., 83-85° C. NMR (CDCl$_3$): $\delta$7.72 (t, 1H); $\delta$7.20 (d, 1H); $\delta$6.83 (d, 1H).

The following were prepared analogously and analyzed by nmr spectroscopy: 2-azido-6-bromopyridine, m.p. 106°–110° C.; 2-azido-6-fluoropyridine, m.p. 45°–48° C.; 2-azido-6-(trifluoromethyl)pyridine, brown oil; 3-azido-5-(trifluoromethyl)pyridine, dark oil; 4-azido-2,3,5,6-tetrachloropyridine, light brown solid.

EXAMPLE 3

Preparation of 2-Azido-5-(trifluoromethyl)pyridine and Certain Analogs

2-Chloro-5-trifluoromethylpyridine (10 g, 55 mmol) was added to a slurry of 5.41 g (80 mmol) of sodium azide in 125 ml of dimethyl sulfoxide. The mixture was heated at between 65°–70° C. for about two days. The mixture was cooled, poured into water, and extracted with ether. The ether extract was washed with water, dried over magnesium sulfate, and stripped of solvent to yield 6.7 g (64 percent of theory) of yellow solid product; m.p., 65°–68° C. NMR (CDCl$_3$): δ9.41 (s, 1H); δ8.40 (d, 1H); δ8.02 (d, 1H).

The following were prepared analogously and analyzed by nmr spectroscopy: 2-azido-4-(trifluoromethyl)pyridine, off white crystals (from 2-fluoro-4-(trifluoromethyl)pyridine; and 2-azido-4,6-bis(trifluoromethyl)pyridine, pale yellow oil crystallizing on standing (from 2-chloro-4,6-bis(trifluoromethyl)pyridine.

EXAMPLE 4

Preparation of 3-Azidopyridine

3-Aminopyridine (18.89 g, 0.20 mol) was added to a warm (55° C.) solution of 36 ml of concentrated sulfuric acid in 210 ml of water. The mixture was stirred for five minutes and was then cooled to 5° C. and a solution of 16.66 g (0.24 mol) of sodium nitrite in 140 ml of water was added dropwise, keeping the temperature below 6° C. The mixture was left to stir for 20 minutes. Urea (2.4 g, 0.04 mol) was added and the mixture was again left to stir at 5° C. for 20 minutes. A solution of 15.60 g (0.24 mol) of sodium azide in 150 ml of water was added, keeping the temperature below 10° C. Nitrogen was immediately evolved. The mixture was stirred at ambient temperature for 1.5 hours after the addition was complete and was then neutralized to pH 6–7 with sodium bicarbonate and extracted with ether. The ether extract was dried over magnesium sulfate and stripped of solvent to yield 21.5 g (89 percent of theory) of dark oil. NMR (CDCl$_3$): δ8.58 (m, 2H) δ7.47 (m, 2H).

EXAMPLE 5

Preparation of Methyl 1-(6-Chloro-2-pyridinyl)-1,2,3-triazole-4-carboxylate, its 5-Isomer, and Certain Analogs A mixture of 6.00 g (40 mmol) of 2-azido-6-chloropyridine and 4.90 g (60 mmol) of methyl propiolate in 50 ml of chloroform was heated at reflux in the dark. After 10 days, the mixture was stripped of solvent and the residue triturated in hot hexane and recovered by filtration. The insoluble solid (4-isomer) was recrystallized from methanol to obtain 8.6 g of off-white fluffy crystals; m.p., 134°–136° C. NMR (CDCl$_3$): δ9.18 (s, 1H); δ8.22 (d, 1H); δ7.96 (t, 1H); δ7.41 (d, 1H); δ3.72 (s, 3H).

Analysis: Calcd. for C$_9$H$_7$ClN$_4$O$_2$: C, 45.30; H, 2.96; N, 23.48. Found: C, 45.45; H, 2.89; N, 23.71.

The hexane solution was stripped of solvent and the residue was recrystallized from hexane to yield 0.4 g of off-white powder (85:15 mixture of 5- to 4-isomers); m.p., 64.5°–68° C. NMR (CDCl$_3$) (only the 5-isomer peaks are recorded for simplicity): δ8.31 (s, 1H); δ8.08 (d, 1H); δ7.90 (d, 1H); δ7.66 (d, 1H).

Analysis: Calcd. for C$_9$H$_7$ClN$_4$O$_2$: C, 45.30; H, 2.96; N, 23.48. Found: C, 45.12; H, 3.05; N, 23.72.

The total yield of both isomers was 97 percent of theoretical.

The following were prepared analogously and identified by nmr spectroscopy and in some cases elemental (CHN) analysis: ethyl 1-(6-bromo-2-pyridinyl)-1,2,3-triazole-4-carboxylate, m.p. 116°–118° C., and its 5-isomer (brown oil); ethyl 1-(6-fluoro-2-pyridinyl)-1,2,3-triazole-4(and 5)-carboxylate, m.p. 80°–87° C.; ethyl 1-(6-(trifluoromethyl)-2-pyridinyl)-1,2,3-triazole-4-carboxylate, m.p. 98°–100° C., and its 5-isomer; ethyl 1-(4-(trifluoromethyl)-2-pyridinyl-1,2,3-triazole-4(and 5)-carboxylate, m.p. 95°–98° C.; and ethyl 1-(4,6-bis(trifluoromethyl)-2-pyridinyl)-1,2,3-triazole-4(and 5)-carboxylate, white powder.

EXAMPLE 6

Preparation of 1-(6-Chloro-2-pyridinyl)-1,2,3-triazole-4-carboxylic Acid and Certain Analogs A slurry of ground potassium hydroxide (85 percent, 2.07 g, 31.4 mmol) in 50 ml of isopropyl alcohol was cooled to 5° C. and to this was added, in one portion, 3.75 g (15.7 mmol) of methyl 1-(6-chloro-2-pyridinyl)-1,2,3-triazole-4-carboxylate. The mixture was stirred for three hours at which time the temperature was allowed to increase to room temperature. The mixture was then poured into cold water and acidified with concentrated hydrochloric acid. The resulting precipitate was filtered, washed with water and ether, and dried overnight under reduced pressure at 50° C. The filtrate was extracted with methylene chloride and the extract was dried over magnesium sulfate and stripped of solvent to obtain more solid. The two solid samples were combined to yield 3.3 g (94 percent of theory) of white powdery solid product; m.p., 144°–145° C. (decomp.). NMR (CDCl$_3$/DMSO) δ9.28 (s, 1H); δ8.34 (d, 2H); δ7.81 (m, 1H).

Analysis: Calcd. for C$_8$H$_7$ClN$_4$O$_3$: C, 39.60; H, 2.91; N, 23.09. Found: C, 39.04; H, 2.99; N, 23.29.

The following were prepared analogously and analyzed by nmr spectroscopy: 1-(6-bromo-2-pyridinyl)-1,2,3-triazole-4-carboxylic acid, m.p. 110°–140° C. (dec.); 1-(6-fluoro-2-pyridinyl)-1,2,3-triazole-4(and 5)-carboxylic acid, m.p. 119°–122° C.; 1-(6-(trifluoromethyl)-2-pyridinyl)-1,2,3-triazole-4(and 5)-carboxylic acid, white solid; 1-(4-(trifluoromethyl)-2-pyridinyl)-1,2,3-triazole-4-carboxylic acid, m.p. 142°–143° C. (dec.); 1-(4,6-bis(trifluoromethyl)-2-pyridinyl)-1,2,3-triazole-4-carboxylic acid, off-white powder.

EXAMPLE 7

Preparation of 2-chloro-6-(1H-1,2,3-triazol-1-yl)pyridine and Certain Analogs A mixture of 2.0 g (8.9 mmol) of 1-(6-chloro-2-pyridinyl)-1,2,3,-triazole-4-carboxylic acid and 50 ml of xylene were heated at reflux for five hours. The mixture was cooled and filtered and the filtrate was stripped of solvent. The residue was extracted with boiling hexane with some methylene chloride added. The extract was stripped of solvent and the residue was sublimed (80°–90° C. at 0.05 mmHg) to obtain 0.76 g (47 percent of theory) of white solid product; m.p., 95°–98° C. NMR (CDCl$_3$) δ8.72 (s, 1H); δ8.30 (d, 1H); δ8.01 (t, 1H); δ7.98 (s, 1H); δ7.49 (d, 1H).

Analysis: Calcd. for C$_7$H$_5$ClN$_4$: C, 46.66; H, 2.79; N, 31.03. Found: C, 46.63; H, 2.60; N, 30.86.

The following were prepared analogously and analyzed by nmr spectroscopy and in most cases elemental (CHN) analysis: 2-bromo-6-(1H-1,2,3-triazol-1-yl)pyridine, m.p. 118°–120° C.; 2-fluoro-6-(1H-1,2,3-triazol-1-yl)pyridine, m.p. 125°–128° C.; 6-(trifluoromethyl)-2-(1H-1,2,3-triazol-1-yl)pyridine, m.p. 50°–51° C.; 4-(trifluoromethyl)-2-(1H-1,2,3-triazol-1-yl)pyridine, m.p. 54°–56° C.; 2,4-bis(trifluoromethyl)-6-(1H-1,2,3-triazol-1-yl)pyridine, m.p. 113°–115° C.; and 2,6-bis(trifluoromethyl)-4-(1H-1,2,3-triazol-1-yl)pyridine, m.p. 81°–81.5° C.

EXAMPLE 8

Preparation of 5-(trifluoromethyl)-2-(1H-1,2,3-triazol-1-yl)pyridine and Certain Analogs A mixture of 6.60 g (35 mmol) of 2-azido-5-(trifluoromethyl)pyridine and 40 ml of vinyl acetate was heated at reflux for six weeks. The mixture was cooled and poured into a mixture of saturated sodium bicarbonate and ice. The mixture was extracted with ether. The ether solution was filtered through a pad of silica gel and stripped of solvent. The residue was extracted with boiling hexane and the hexane extract concentrated under reduced pressure. The residue was subjected to sublimation to remove unreacted starting material and the remaining material was recrystallized from hexane to yield 0.45 g (6 percent of theory) of off-white needles; m.p, 111°–112.5° C. NMR (CDCl$_3$): δ8.92 (s, 1H); δ8.80 (s, 1H); δ8.31 (m, 1H); δ8.00 (s, 1H).

Analysis: Calcd. for C$_8$H$_5$F$_3$N$_4$: C, 44.87; H, 2.35; N, 26.16. Found: C, 44.94; H, 2.47; N, 25.96.

The following were prepared analogously and identified by NMR spectroscopy and elemental (CHN) analysis: 5-(trifluoromethyl)-3-(1H-1,2,3-triazol-1-yl)pyridine, m.p. 129.5°–131° C.; 3-(1H-1,2,3-triazol-1-yl)pyridine, m.p. 80.5°–83° C.; 2,6-dichloro-4-(1H-1,2,3-triazol-1-yl)pyridine, m.p. 80°–83° C.; 2-chloro-6-(trifluoromethyl)-4-(1H-1,2,3-triazol-1-yl)pyridine, and 2,3,5,6-tetrachloro-4-(1H-1,2,3-triazol-1-yl)pyridine, m.p. 161°–162.5° C.

EXAMPLE 9

Preparation of 2-Methoxy-6-(1H-1,2,3-triazol-1-yl)pyridine

A mixture of 4.00 g (20 mmol) of 2-chloro-6-(1H-1,2,3-triazol-1-yl)pyridine and 8.5 ml of sodium methoxide (25 percent in methanol, 40 mmol) in dimethyl sulfoxide was heated at 80° C. for six hours. The mixture was cooled, poured over ice and extracted with methylene chloride. The extract was dried over magnesium sulfate and stripped of solvent. The solid residue was triturated in a minimal amount of methanol and filtered to yield 0.4 g (10 percent of theory) of tan solid product; m.p., 75°–78° C. NMR (CDCl$_3$): δ8.60 (s, 1H); δ7.94 (m, 3H); δ6.90 (m, 1H); δ4.06 (s, 3H).

Analysis: Calcd. for C$_8$H$_8$N$_4$O: C, 54.54; H, 4.58; N, 31.80. Found: C, 53.90; H, 4.49; N, 31.04.

Additional compounds of Formula I were prepared by using conventional transformations known to those skilled in the art of pyridine chemistry. The products prepared, physical properties, starting materials, and chemical reactions employed are given in the following table. Each compound was identified by NMR and elemental (CHN) analyses.

INTERCONVERSION OF 2-Z-6-(H—1,2,3-TRIAZOL-1-YL)-PYRIDINES

| Z of Product | m.p., °C. | Z of Starting Material | Method |
|---|---|---|---|
| H— | 77–78.5 | Br | Reduction with hydrogen using Pd on C catalyst and triethylamine |
| (CH$_3$)$_2$CHS— | oil slowly solidifying | Br | Displacement with potassium propanethiolate in 2-propanol |
| (CH$_3$)$_2$CHSO$_2$— | 85–87 | (CH$_3$)$_2$CHS— | Oxidation with hypochlorous acid |
| C$_6$H$_{13}$S— | 56–60 | Br | Displacement with potassium hexanethiolate in 2-propanol |
| C$_6$H$_{13}$SO$_2$— | 68–70 | C$_6$H$_{13}$S— | Oxidation with hypochlorous acid |
| —CH$_3$ | n$^D$1.5715 | Br | Alkylation using butyl lithium and methyl iodide |
| —CN | 119–120.5 | F | Displacement with potassium cyanide in dimethyl sulfoxide |
| (CH$_3$)$_2$CHO— | 40.5–42.5 | F | Displacement with sodium 2-propoxide in 2-propanol |
| C$_6$H$_5$O— | 82–84 | F | Displacement with sodium phenoxide in dimethyl sulfoxide |
| CH$_3$S— | 63–65 | F | Displacement with sodium methanethiolate in methanol |

Still other contemplated compounds of Formula I exemplify the invention, including those with the following substituent patterns (Xn, position of triazolyl moiety): 3,5,6-trichloro, 2; 2-chloro-6-allyloxy, 4; 2-cyclopropylmethoxy-4-t-butyl, 6; 2-cyclopentylthio, 5; 2-bromo-3-carboxamido, 6; 4-carbomethoxy, 2; 3-nitro, 4; 2-chloro-4-(trichloromethyl), 6; and the like.

EXAMPLE 10

Aster Leafhopper Control on Rice Plants

Seven to ten rice seedlings about 5 inches in height were grown in individual 4 ounce plastic containers in the greenhouse, using vermiculite as a substrate. Test compounds were prepared as 10,000 ppm acetone concentrates which were diluted to several predetermined concentrations using water containing 0.1 percent Triton X-100 as a surfactant. The foliage of the plants was dipped into the resulting solutions or 25 ml of the solutions were injected into the plant root zone. A plastic cylinder was placed over each of the containers. Each cylinder was then infested with 10 aster leafhoppers (*Macrosteles fascifrons*) and capped with a plastic metal-screened top. A control group was treated in a similar manner using only water and surfactant. Treatments were maintained under greenhouse conditions and mortality readings were made at 72 hours post-infestation. Complete control was observed with a 100 ppm concentration of 6-(trifluoromethyl)-2-(1H-1,2,3-triazol-1-yl)pyridine using either method of application. 2-Chloro-6-(1H-1,2,3-triazol-1-yl)pyridine at 400 ppm gave complete control using the dip method and ten percent control using the soil injection method.

EXAMPLE 11

Aster Leafhopper Control on Artificial Diet

Test compounds were formulated using a 20,000 ppm acetone concentrate and then diluted with distilled water containing 1.0 percent sucrose to give a 400, 100, and 25 ppm dilution series. In some cases, gentle heating was required to dissolve the compounds. Petri-dish bottoms (35×10 mm) were covered with a piece of Parafilm M, which was tightly stretched and adhered to the sides of the dish. Two small pin holes were made on the bottom side of each dish using a Craftsman fine-tipped soldering iron. Five to seven adult aster leafhoppers were placed into 1 ounce clear plastic medicinal caps (with pinholes to allow proper ventilation) and the cups immediately capped with petri-dish bottoms, parafilm side facing the insects. Four ml of the prepared formulations were injected through one of the pinholes on the petri-dish bottoms. Tests were maintained in a bioclimatic chamber under a 14 hour photoperiod at 75°–80° F. and 50 percent relative humidity. Mortality readings were made three days after the exposure time. Four to five replicates were used for each treatment. The results obtained for a number of compounds of Formula I at 400 ppm are given in the following table.

| Aster Leafhopper Control by Compounds of Formula I | | |
|---|---|---|
| *Xn | *Position of Triazole | Percent Control |
| 5-CF$_3$ | 3 | 100 |
| 2-SC$_6$H$_{13}$ | 6 | 27 |
| 2-SO$_2$C$_6$H$_{13}$ | 6 | 65 |
| 2-SO$_2$C$_3$H$_7$ | 6 | 94 |
| n = 0 | 2 | 82 |
| n = 0 | 3 | 65 |
| 2-Cl-6-CF$_3$ | 4 | 100 |
| 2,6-diCl | 4 | 100 |
| 2-F | 6 | 100 |
| 6-CF$_3$ | 2 | 100 |
| 2-Br | 6 | 100 |
| 2-OCH$_3$ | 6 | 100 |
| 2,6-bisCF$_3$ | 4 | 100 |

*See Formula 1

What is claimed is:

1. A (1H-1,2,3-triazol-1-yl)pyridine of the formula

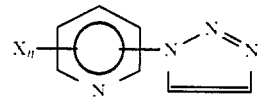

wherein
each X independently represents F, Cl, Br, C$_1$–C$_4$ alkyl, OR$^1$, SR$^1$, SOR$^1$, SO$_2$R$^1$, NH$_2$, NHR$^1$, NR$^1_2$, CY$_3$, CHY$_2$, CN, NO2, CO$_2$R$^2$, or phenoxy containing up to three substituents selected from F, Cl, Br, C$_1$–C$_4$ alkyl, and CF$_3$;
each Y independently represents Cl or F;
R$^1$ represents C$_1$–C$_6$ alkyl, C$_3$–C$_6$ alkenyl, or C$_3$–C$_6$ cycloalkyl;
R$^2$ represents H, C$_1$–C$_6$ alkyl, C$_3$–C$_6$ alkenyl, C$_3$–C$_6$ cycloalkyl; C$_1$–C$_4$ alkoxy C$_2$–C$_3$ alkyl, NH$_2$, NH C$_1$–C$_4$ alkyl, or N(C$_1$–C$_4$ alkyl)$_2$; and
n represents 0, 1, 2, 3, or 4.

2. A compound of claim 1 wherein X represents F, Cl, Br, CH$_3$, OCH$_3$, SCH$_3$, CF$_3$, or CN and n represents 1, 2, or 3.

3. A compound of claim 1 wherein at least one of X represents CF$_3$.

4. A compound of claim 1 wherein at least one of X represents F, Cl, or Br.

5. A compound of claim 1 wherein the triazol-1-yl moiety is at the 2- or 6-position of the pyridine moiety.

6. The compound of claim 5, 2-(1H-1,2,3-triazol-1-yl)-5-(trifluoromethyl)pyridine.

7. The compound of claim 5, 2-(1H-1,2,3-triazol-1-yl)pyridine.

8. The compound of claim 5, 2-fluoro-6-(1H-1,2,3-triazol-1-yl)pyridine.

9. The compound of claim 5, 2-chloro-6-(1H-1,2,3-triazol-1-yl)pyridine.

10. The compound of claim 5, 2-bromo-6-(1H-1,2,3-triazol-1-yl)pyridine.

11. The compound of claim 5, 2-methoxy-6-(1H-1,2,3-triazol-1-yl)pyridine.

12. The compound of claim 5, 2-methylthio-6-(1H-1,2,3-triazol-1-yl)pyridine.

13. The compound of claim 5, 2,4-bis(trifluoromethyl)-6-(1H-1,2,3-triazol-1-yl)pyridine.

14. The compound of claim 1, 3-(1H-1,2,3-triazol-1-yl)pyridine.

15. The compound of claim 1, 3-(1H-1,2,3-triazol-1-yl)-5-(trifluoromethyl)pyridine.

16. The compound of claim 1, 2,6-dichloro-4-(1H-1,2,3-triazol-1-yl)pyridine.

17. The compound of claim 1, 2,6-bis(trifluoromethyl)-4-(1H-1,2,3-triazol-1-yl)pyridine.

* * * * *